United States Patent
Govari et al.

(10) Patent No.: US 11,497,566 B2
(45) Date of Patent: Nov. 15, 2022

(54) LOOSE MODE FOR ROBOT

(71) Applicant: Biosense Webster (Israel) Ltd., Yokneam (IL)

(72) Inventors: Assaf Govari, Haifa (IL); Vadim Gliner, Haifa (IL)

(73) Assignee: Biosense Webster (Israel) Ltd., Yokneam (IL)

(*) Notice: Subject to any disclaimer, the term of this patent is extended or adjusted under 35 U.S.C. 154(b) by 961 days.

(21) Appl. No.: 16/171,996

(22) Filed: Oct. 26, 2018

(65) Prior Publication Data
US 2020/0129246 A1 Apr. 30, 2020

(51) Int. Cl.
A61B 34/30 (2016.01)
A61B 34/20 (2016.01)
G06T 7/00 (2017.01)

(52) U.S. Cl.
CPC .............. *A61B 34/30* (2016.02); *A61B 34/20* (2016.02); *G06T 7/0012* (2013.01); *A61B 2034/2051* (2016.02); *A61B 2034/301* (2016.02); *A61B 2034/302* (2016.02); *G06T 2207/10081* (2013.01); *G06T 2207/10116* (2013.01); *G06T 2207/30008* (2013.01)

(58) Field of Classification Search
CPC . A61B 34/30; A61B 34/20; A61B 2034/2051; A61B 2034/301; A61B 2034/302; A61B 2034/2074; A61B 2034/743; A61B 2034/744; A61B 2090/036; A61B 2090/065; A61B 90/50; A61B 34/25; A61B 2034/105; A61B 34/70; G06T 7/0012; G06T 2207/10081; G06T 2207/10116; G06T 2207/30008

USPC ......................................................... 700/245
See application file for complete search history.

(56) References Cited

U.S. PATENT DOCUMENTS 6,132,368 A 10/2000 Cooper
10,646,280 B2 * 5/2020 Crawford ............... A61B 90/96
(Continued)

FOREIGN PATENT DOCUMENTS

CN 104972473 10/2015
KR 101911843 10/2018
WO WO 2018/0125917 7/2018

OTHER PUBLICATIONS

European Search Report dated Feb. 6, 2020 from corresponding European Patent Application No. 19205269.4.

*Primary Examiner* — Jerome Grant, II
(74) *Attorney, Agent, or Firm* — Todd J. Burns

(57) ABSTRACT

A robotic arm control system including a medical instrument to be inserted into a body-part, a force sensor to detect force applied by the instrument to the body-part, a robotic arm attached to the instrument, a first position sensor to track an instrument position of the instrument in the body-part, a second position sensor to track a body position of the body-part, and a controller to compute, responsively to the instrument position and the body position, a location of the instrument relative to the body-part, compare the detected force applied by the instrument to a permitted force level for application to an anatomical feature at the computed location and send a control command to, or cut power of, the robotic arm to loosen a rigidity of at least one robotic joint in response to the detected force applied by the instrument being greater than the permitted force level.

17 Claims, 6 Drawing Sheets

(56) References Cited

U.S. PATENT DOCUMENTS

| | | | |
|---|---|---|---|
| 11,298,186 B2* | 4/2022 | Chou | A61B 17/3423 |
| 2006/0161138 A1 | 7/2006 | Orban et al. | |
| 2007/0100332 A1 | 5/2007 | Paul et al. | |
| 2008/0114388 A1 | 5/2008 | Culp et al. | |
| 2009/0093806 A1 | 4/2009 | Govari et al. | |
| 2015/0053749 A1 | 2/2015 | Shelton et al. | |
| 2016/0007842 A1 | 1/2016 | Govari et al. | |
| 2016/0361125 A1* | 12/2016 | Balicki | A61B 34/30 |
| 2017/0056112 A1 | 3/2017 | Gliner et al. | |
| 2017/0151027 A1 | 6/2017 | Walker et al. | |
| 2019/0000447 A1* | 1/2019 | Shelton, IV | A61B 34/37 |
| 2019/0059973 A1* | 2/2019 | Shelton, IV | A61B 18/1206 |
| 2019/0201145 A1* | 7/2019 | Shelton, IV | A61B 90/90 |
| 2019/0274716 A1* | 9/2019 | Nott | A61B 5/068 |
| 2020/0289227 A1* | 9/2020 | Jiang | A61B 34/76 |
| 2021/0085316 A1* | 3/2021 | Harris | G16H 40/63 |
| 2021/0138198 A1* | 5/2021 | Leo | A61M 25/0158 |
| 2021/0196397 A1* | 7/2021 | Peng | A61B 34/37 |
| 2022/0104806 A1* | 4/2022 | Shelton, IV | A61B 17/0686 |
| 2022/0104821 A1* | 4/2022 | Shelton, IV | A61B 17/07207 |
| 2022/0104910 A1* | 4/2022 | Shelton, IV | A61B 1/00009 |

* cited by examiner

LOOSE MODE FOR ROBOT

FIELD OF THE INVENTION

The present invention generally relates to control of robots, and in particular, but not exclusively, relates to control of robots during medical procedures.

BACKGROUND

By way of introduction, a medical instrument may be used in brain surgery or sinus dilation among other applications. In sinus dilation, a medical instrument may be inserted via the nasal cavity through various sinus cavities. In brain surgery, instead of opening skull to remove a tumor, a medical tool may be inserted via the nasal cavity and the sinus cavities. Robotic arms may be useful in such applications to hold the medical instrument.

U.S. Pat. No. 6,132,368 to Cooper describes systems and methods for performing robotically-assisted surgical procedures on a patient. In particular, a three-component surgical system is provided that includes a non-sterile drive and control component, a sterilizable end effector or surgical tool and an intermediate connector component that includes mechanical elements for coupling the surgical tool with the drive and control component and for transferring motion and electrical signals therebetween. The drive and control component are shielded from the sterile surgical site, the surgical tool is sterilizable and disposable and the intermediate connector is sterilizable and reusable. In this manner, the intermediate connector can be sterilized after a surgical procedure without damaging the motors or electrical connections within the drive and control component of the robotic system.

US Published Patent Application 2006/0161138 of Orban, et al., describes a sterile drape with integrated sterile adaptor, a telerobotic surgical system, and a method of use are provided for draping portions of a telerobotic surgical system to maintain a sterile barrier between the sterile surgical field and the non-sterile robotic system while also providing an interface for transferring mechanical and electrical energy and signals.

US Published Patent Application 2008/0114388 of Culp, et al., describes a surgical tool system including a handpiece with a power generating unit and a control console for supplying energization signals to the power generating unit. Based on the data in a memory associated with the handpiece, the control console supplies energization signals to the handpiece power generating unit in either a motor drive mode or a direct drive mode. In the motor drive mode the signals are supplied to windings integral with the power generating unit based on the position of a rotor also part of the power generating unit. In the direct drive mode, energization signals are supplied to the power generating unit independent of rotor position.

US Published Patent Application 2015/0053749 of Shelton, et al., describes a surgical instrument system comprising a surgical instrument and an end effector, wherein the end effector comprises a distal end, a proximal connection portion configured to attach the end effector to the surgical instrument, a first jaw, and a second jaw movable relative to the first jaw, wherein the second jaw is movable between an open orientation, a partially-closed orientation, and a closed orientation. The end effector can further comprise at least one sensor configured to detect the orientation of the second jaw and an array of indicators configured to simulate the orientation of the second jaw.

SUMMARY

There is provided in accordance with an embodiment of the present disclosure a robotic arm control system including a medical instrument configured to be reversibly inserted into a body-part of a living subject, a force sensor configured to detect a force applied by the medical instrument to the body-part, a robotic arm attached to the medical instrument, the robotic arm including a plurality of robotic joints configured to control movement of the robotic arm and manipulate the medical instrument, a first position sensor configured to track an instrument position of the medical instrument in the body-part, a second position sensor disposed on the living subject and configured to track a body position of the body-part during the insertion of the medical instrument in the body-part, and a controller configured to compute, responsively to the instrument position and the body position, a location of the medical instrument relative to the body-part, compare the detected force applied by the medical instrument to a permitted force level for application to an anatomical feature at the computed location, and send a control command to, or cut power of, the robotic arm to loosen a rigidity of at least one robotic joint of the plurality of robotic joints in response to the detected force applied by the medical instrument at the computed location being greater than the permitted force level.

Further in accordance with an embodiment of the present disclosure the force sensor is disposed on the medical instrument.

Still further in accordance with an embodiment of the present disclosure the controller is configured to set the permitted force level for application to the anatomical feature.

Additionally, in accordance with an embodiment of the present disclosure the controller is configured to register a medical scan with respect to at least one given location of the body-part, the medical scan including an image of the anatomical feature, and identify that the anatomical feature is at the computed location of the medical instrument based on the registration of the medical scan and the instrument position.

Moreover, in accordance with an embodiment of the present disclosure controller is configured to set the permitted force level for application to the anatomical feature based on an identification of the anatomical feature.

Further in accordance with an embodiment of the present disclosure the image of the anatomical feature has a radiodensity, and the controller is configured to set the permitted force level for application to the anatomical feature based on the radiodensity of the image of the anatomical feature.

Still further in accordance with an embodiment of the present disclosure the controller is configured to identify a tissue type of the anatomical feature based on the radiodensity of the image of the anatomical feature, and set the permitted force level for application to the anatomical feature based on the tissue type of the anatomical feature.

Additionally, in accordance with an embodiment of the present disclosure the controller is configured to send a control command to the robotic arm to drop the medical instrument in response to the detected force applied by the medical instrument at the computed location being greater than the permitted force level.

There is also provided in accordance with still another embodiment of the present disclosure a robotic arm control method including controlling movement of a robotic arm attached to a medical instrument, which is reversibly inserted into a body-part of a living subject, detecting a force applied by the medical instrument to the body-part, tracking an instrument position of the medical instrument in the body-part, tracking a body position of the body-part during the insertion of the medical instrument in the body-part, computing, responsively to the instrument position and the body position, a location of the medical instrument relative to the body-part, comparing the detected force applied by the medical instrument to a permitted force level for application to an anatomical feature at the computed location, and sending a control command to, or cutting power of, the robotic arm to loosen a rigidity of at least one robotic joint of the robotic arm in response to the detected force applied by the medical instrument at the computed location being greater than the permitted force level.

Moreover, in accordance with an embodiment of the present disclosure the detecting the force is performed by a force sensor that is disposed on the medical instrument.

Further in accordance with an embodiment of the present disclosure, the method includes setting the permitted force level for application to the anatomical feature.

Still further in accordance with an embodiment of the present disclosure, the method includes registering a medical scan with respect to at least one given location of the body-part, the medical scan including an image of the anatomical feature, and identifying that the anatomical feature is at the computed location of the medical instrument based on the registration of the medical scan and the instrument position.

Additionally, in accordance with an embodiment of the present disclosure the setting the permitted force level for application to the anatomical feature is based on an identification of the anatomical feature.

Moreover, in accordance with an embodiment of the present disclosure the image of the anatomical feature has a radiodensity, and the setting the permitted force level for application to the anatomical feature is based on the radiodensity of the image of the anatomical feature.

Further in accordance with an embodiment of the present disclosure, the method includes identifying a tissue type of the anatomical feature based on the radiodensity of the image of the anatomical feature, and wherein the setting the permitted force level for application to the anatomical feature is based on the tissue type of the anatomical feature.

Still further in accordance with an embodiment of the present disclosure the sending includes sending a control command to the robotic arm to drop the medical instrument in response to the detected force applied by the medical instrument at the computed location being greater than the permitted force level.

There is also provided in accordance with still another embodiment of the present disclosure a software product, including a non-transient computer-readable medium in which program instructions are stored, which instructions, when read by a central processing unit (CPU), cause the CPU to control movement of a robotic arm attached to a medical instrument, which is reversibly inserted into a body-part of a living subject, store a detected force applied by the medical instrument to the body-part, store an instrument position of the medical instrument in the body-part, store a body position of the body-part during the insertion of the medical instrument in the body-part, compute, responsively to the instrument position and the body position, a location of the medical instrument relative to the body-part, compare the detected force applied by the medical instrument to a permitted force level for application to an anatomical feature at the computed location, and send a control command to, or cut power of, a robotic arm to loosen a rigidity of at least one robotic joint of the robotic arm in response to the detected force applied by the medical instrument at the computed location being greater than the permitted force level.

BRIEF DESCRIPTION OF THE DRAWINGS

The present invention will be understood from the following detailed description, taken in conjunction with the drawings in which.

DESCRIPTION OF EXAMPLE EMBODIMENTS

Overview

Figure 1:
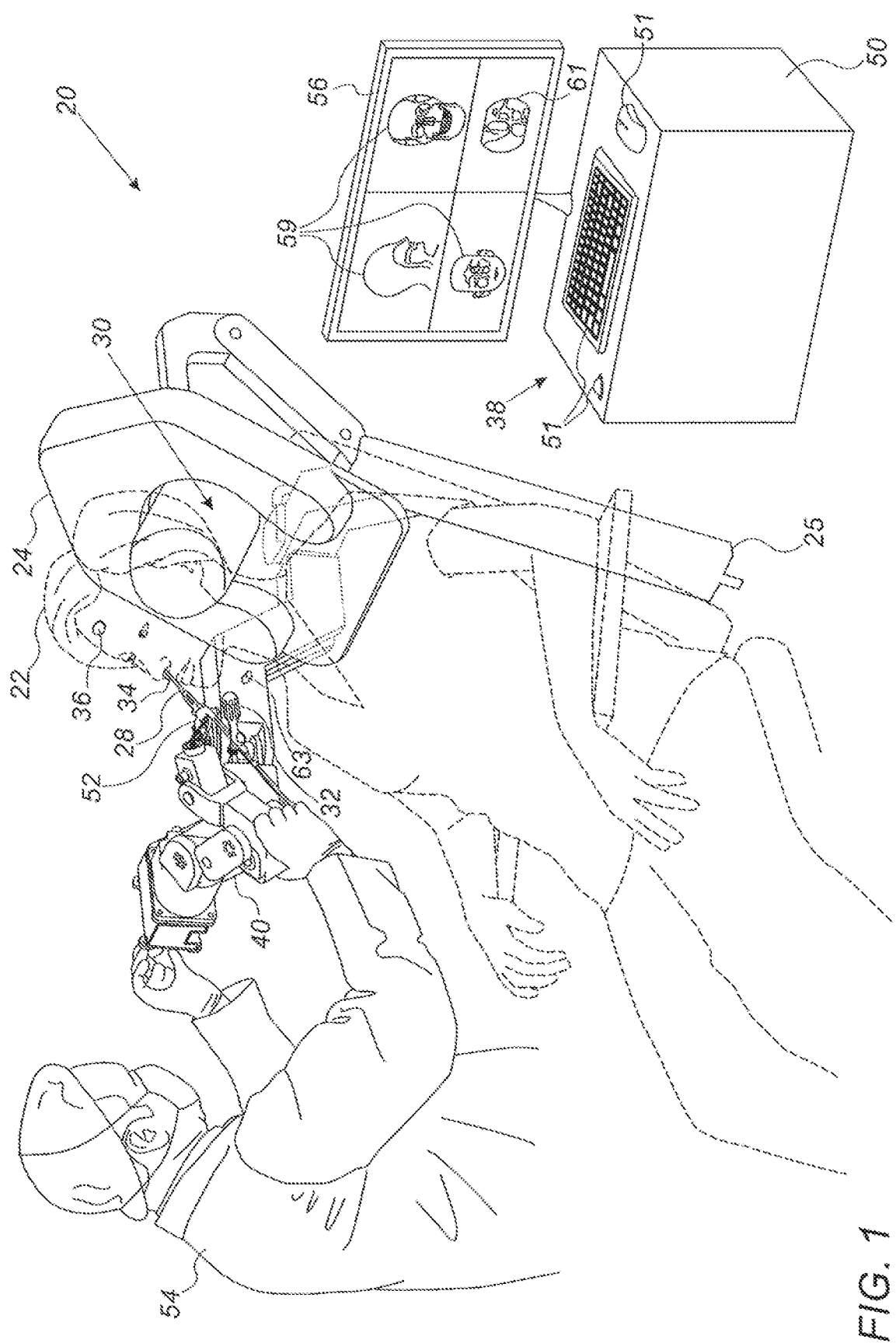
FIG. 1 is a schematic illustration of a robotic medical procedure system, according to an embodiment of the present invention.

By way of introduction, a medical instrument may need to be carefully maneuvered by a physician during a medical procedure. The physician may need both hands free for other surgical tasks. In some circumstances, the physician may ask his assistant to hold and guide the medical instrument. The task of holding and guiding the instrument may be challenging to perform accurately and quickly. Robots may ease this task by grasping the medical instrument and holding it in place when required, thereby making handling somewhat easier. However, robots may also pose a hazard in certain situations when the parameters under which the robot operates go outside the specifications for the robot. For example, during an ear-nose and throat (ENT) procedure using a robotic arm to hold the medical instrument, which is already positioned in a patient, the robotic arm may not be able to correctly deal with a large subsequent movement of the patient. In such cases, the robotic arm may attempt to adjust the position of the medical instrument, but the adjustment may be incorrect and may cause trauma to the patient.

In embodiments of the present invention, a system includes a controller that sends a control command to a robotic arm, which is holding a medical instrument, to loosen a rigidity of at least one robotic joint of the robotic arm. The control command is sent in response to detecting that a force applied by the medical instrument to a body-part is greater than a permitted force level on an anatomical feature of the body-part at the location of the medical instrument. In some embodiments, the power to the robotic arm may be cut on detecting excessive force.

Loosening the rigidity of the robotic arm, sometimes known as "loose" mode, allows the physician to manually move or remove the medical instrument. Additionally, if the patient moves when robot is in "loose" mode the medical instrument typically moves with the patient without causing trauma, or causing less trauma, to the patient.

For example, if the medical instrument is inserted in the sinus ostium, the medical instrument may be near the optic nerve when the patient moves his head. In such an instant, the system senses that the force applied by the medical instrument is excessive in the region of the optic nerve and therefore sends a control command to place the robotic arm in to "loose" mode.

Identification of anatomical features may be performed using a medical scan, such as a CT scan or other scan data, which is registered with the system. The medical scan may provide an indication of various anatomical features such as bone, soft tissue, blood, organs, nerves etc. The indication of the various anatomical features may be based on various radiodensity values, such as Hounsfield units (HU), in the scan, by way of example only. Additionally, or alternatively, anatomical features, such as the optic nerve or brain, may be identified in the medical scan automatically using image analysis or manually by a skilled operator or radiologist. The identified anatomical features may then be registered with the system.

In some embodiments, the system also includes suitable position sensors to sense positions of the body-part and the medical instrument, as well as at least one force sensor disposed on the medical instrument to detect a force applied by the medical instrument on a body-part of the patient. The controller computes a relative location of the medical instrument with respect to the body-part based on the sensed positions of the body-part and the medical instrument.

The controller may identify that an anatomical feature is at the computed location of the medical instrument based on the registration of the medical scan and the instrument position. The controller may identify a tissue type (e.g., bone, soft tissue, fat, or blood) of the anatomical feature based on the radiodensity of an image of the anatomical feature in the medical scan. The term "at the computed location" used in the specification and claims is defined to include an anatomical feature within a given distance of the computed location measured in any suitable unit of measurement. For example, when operating within a patient's head, where there are many fine, sensitive anatomical structures, an anatomical feature may be considered to be "at the computed location" if its position in the medical scan is within 1 mm of the computed location of the medical instrument, or possibly within a greater distance, such as 3 mm. In other parts of the body, the tolerances may be greater.

The controller sets a permitted force level for application to the anatomical feature based on the identified tissue type or the identification (e.g., optic nerve or brain) of the anatomical feature. For example, a higher force is permitted against bone than against soft-tissue or the optic nerve.

The controller compares the detected force applied by the medical instrument to a permitted force level for application to the anatomical feature at the computed location and send a control command to the robotic arm (which may include cutting power to the robotic arm) to loosen a rigidity of at least one robotic joint of the robotic arm when the detected force applied by the medical instrument at the computed location is greater than the permitted force level. The loose mode may even lead to the robot dropping the medical instrument, but this inconvenience is generally more acceptable compared to the risk of trauma.

In the embodiments described below, the force sensors are generally disposed on the medical instrument and not on the robotic arm. Force sensors disposed on the robotic arm may not provide an accurate force reading due to the weight of the robotic arm. In cases where another medical instrument is used, such as a suction tool, the suction tool may create an inaccurate false force reading of the force applied by the medical instrument when the force sensors are disposed on the robotic arm. In some case, however, a force sensor may be disposed on the robotic arm instead of, or in addition to, that on the medical instrument.

Although the embodiments describe below refer specifically to procedure performed within a patient's nasal and sinus cavities, the principles of the present invention may similarly be applied, mutatis mutandis, in other sorts of robotic surgery, both within the head and in other parts of the body. All such alternative embodiments are considered to be within the scope of the present invention.

System Description

Documents incorporated by reference herein are to be considered an integral part of the application except that, to the extent that any terms are defined in these incorporated documents in a manner that conflicts with definitions made explicitly or implicitly in the present specification, only the definitions in the present specification should be considered.

Figure 2:
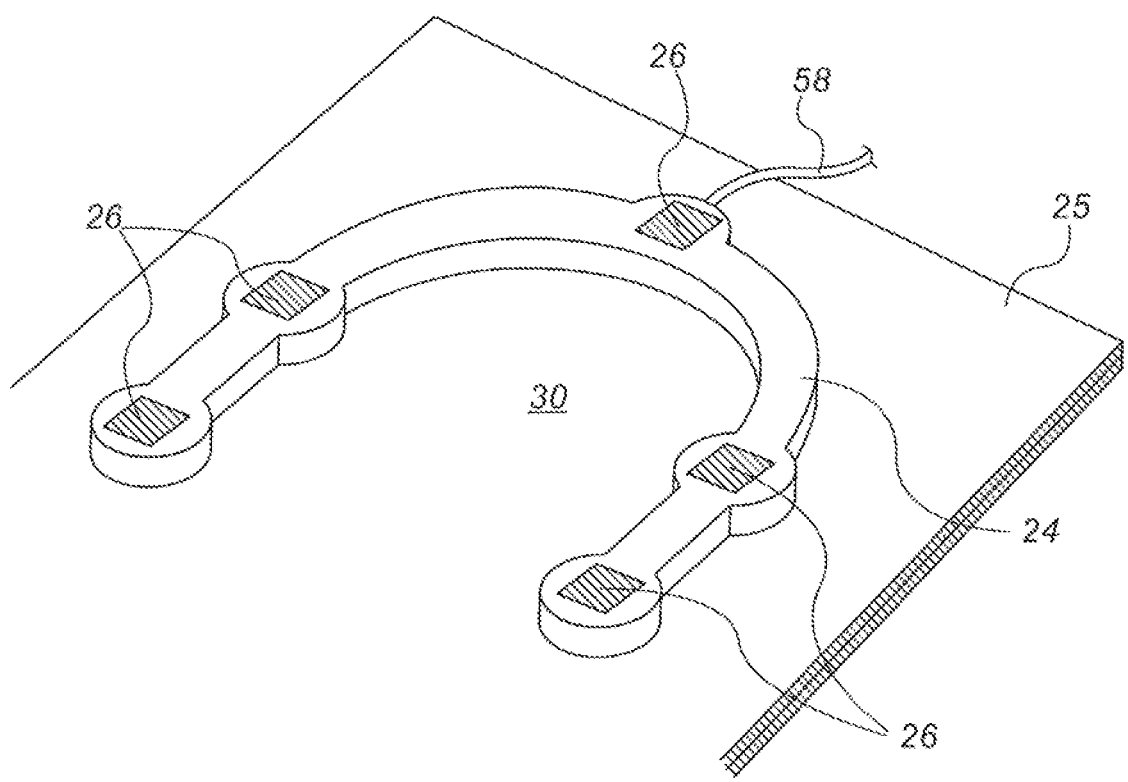
FIG. 2 is a schematic illustration of a magnetic field radiation assembly used in the robotic medical procedure system, according to an embodiment of the present invention.

Turning now to the drawings, reference is now made to FIG. 1, which is a schematic illustration of a robotic medical procedure system 20, and to FIG. 2, which is a schematic illustration of a magnetic field radiation assembly 24 used in the system 20, according to an embodiment of the present invention. The robotic medical procedure system 20 is typically used during an invasive and/or investigative procedure on a nasal sinus or another body part (such as the brain) of a patient 22.

For the procedure, the magnetic field radiation assembly 24 may be positioned behind and/or around the head of the patient 22, for example by fixing the assembly 24 to a chair 25 (or bed) upon which the patient is sitting (or lying). The magnetic field radiation assembly 24 in the pictured example comprises five magnetic field radiators 26, which are fixed in a horseshoe shaped frame, the frame being positioned beneath or around the patient 22 so that the magnetic field radiators 26 surround the head of the patient 22. Alternatively, smaller or larger numbers of radiators 26 may be used, in various different configurations. The magnetic field radiators 26 are configured to radiate alternating magnetic fields at respective frequencies into a region 30, in proximity to the magnetic field radiation assembly 24 and which includes the head of patient 22. The alternating magnetic fields induce signals in a position sensor 32 and a position sensor 36. The position sensor 32 is shown disposed on a medical instrument 28 in order to track a position of the medical instrument 28. By way of example only, the medical instrument 28 may include any one or more of the following, a probe for inserting into the body-part, an endoscope, and/or a surgical tool such as an ENT tool, suction tool, microdebrider, or a shaver.

The medical instrument 28 is attached to and held by a robotic arm 40, which is configured to manipulate the medical instrument 28. The robotic arm 40 includes a plurality of robotic joints configured to control movement of the robotic arm 40 and manipulate the medical instrument 28.

The position sensor 36 is shown disposed on the patient 22 (e.g., on the forehead of the patient 22 or any other suitable body part) in order to track a position of the patient 22 (e.g., to track a position of the head of the patient 22).

Each position sensor 32, 36 typically includes a set of three orthogonal coils, and the signals may be analyzed by a controller 38 to derive the location and orientation of the position sensors 32, 36 with respect to the magnetic field radiation assembly 24. It will be understood that the location and orientation of position sensors 32, 36 may be determined for substantially any positioning of the position sensor within region 30. Although the position sensors 32, 36 are described herein as magnetic position sensors, the positions of the medical instrument 28 and the patient 22 may be computed using any suitable position sensing technology, for example, but not limited to, electrical, ultrasonic, optical, inertial, or any other suitable type known in the art.

As is described in more detail below, position sensor 32 is affixed to the medical instrument 28, and determination of the location and orientation of the position sensor 32 enables the location and orientation of a distal end 34 (or other location) of the medical instrument 28, that may be reversibly inserted into a body-part of the patient 22 (the living subject), to be tracked. When the medical instrument 28 is a rigid medical instrument, the position sensor 32 may generally be disposed on any suitable part of the medical instrument 28 (e.g., the distal end 34 or on a proximal end 52 of the medical instrument 28) and/or on the robotic arm 40 which is holding the medical instrument 28. If the distal end 34 of the medical instrument 28 is flexible, the position sensor 32 is generally disposed on the distal end 34 of the medical instrument 28 in order to accurately track the position of the distal end 34 of the medical instrument 28.

Similarly, determination of the location and orientation of the position sensor 36 enables the location and orientation of the body-part (e.g., head) of the patient 22 to be tracked. The position sensor 36 is shown in FIG. 1 as being disposed on the forehead of the patient 22. The position sensor 36 may be disposed on any other suitable body part of the patient 22 in order to track the position/movement of the patient 22.

A system using magnetic field radiators, such as the magnetic field radiators 26, for tracking an entity inserted into a patient is described in US Patent Publication 2016/0007842, of Govari et al., which is incorporated herein by reference. In addition, the Carto® system produced by Biosense Webster of 33 Technology Drive, Irvine, Calif. 92618 USA, uses a tracking system similar to that described herein for finding the location and orientation of a coil in a region irradiated by magnetic fields.

The robotic arm 40 generally has its own robotic coordinate system. The robotic coordinate system is registered with a magnetic coordinate system of the magnetic field radiators 26 and/or vice-versa. Registration of the robotic coordinate system with the magnetic coordinate system may be performed, for example, by moving the robotic arm 40, or the medical instrument 28 attached to the robotic arm 40, to one or more locations known to the magnetic field radiators 26, for example, to a location on the magnetic field radiation assembly 24 or to the position sensor 36 or to one or more other known locations on the patient 22. Once registration of the robotic coordinate system with the magnetic coordinate system has been performed, locations in the magnetic coordinate system can be translated to the robotic coordinate system in order to manipulate the robotic arm 40 correctly.

Elements of system 20, including radiators 26, may be controlled by the controller 38, which comprises a processing unit communicating with one or more memories. Typically, the elements may be connected by cables to the controller 38, for example, radiators 26 may be connected by a cable 58 to the controller 38. Alternatively, or additionally, the elements may be coupled wirelessly to the controller 38. The controller 38 may be mounted in a console 50, which comprises operating controls 51 that typically include a keypad and/or a pointing device such as a mouse or trackball. The console 50 also connects to other elements of the robotic medical procedure system 20, such as the proximal end 52 of the medical instrument 28. A physician 54 uses the operating controls 51 to interact with the controller 38 while performing the procedure, and the controller 38 may present results produced by system 20 on a display screen 56. In FIG. 1, the display screen 56 is displaying various views 59 of a previous CT scan (or other suitable scan) which may be used as an aid for the physician 54 to guide the medical instrument 28 in the body-part. The display screen 56 also shows an image 61 captured by the medical instrument 28.

In practice, some or all of these functions of the controller 38 may be combined in a single physical component or, alternatively, implemented using multiple physical components. These physical components may comprise hard-wired or programmable devices, or a combination of the two. In some embodiments, at least some of the functions of the processing circuitry may be carried out by a programmable processor under the control of suitable software. This software may be downloaded to a device in electronic form, over a network, for example. Alternatively, or additionally, the software may be stored in tangible, non-transitory computer-readable storage media, such as optical, magnetic, or electronic memory.

The robotic medical procedure system 20 may optionally include a lens cleaning device 63 configured to clean a lens of an endoscope when an endoscope is included in the medical instrument 28. The lens cleaning device 63 may comprise a water jet sprayer for spraying water on the lens or a wiper to wipe the lens with a suitable material, for example, but not limited to, a piece of gauze. The lens cleaning device 63 may be disposed on the robotic arm 40. Alternatively, or additionally, the lens cleaning device 63 may be implemented as part of the medical instrument 28, for example, with a jet spray, which may be activated when the medical instrument 28 is removed from the body-part.

FIGS. 3A-C, 4, 5 describe the medical instrument 28 as a rigid medical instrument and the position sensor 32 as a movable position sensor which may be fixed to any suitable part of the medical instrument 28 and therefore the location of the position sensor 32 does not initially indicate the distal end 34 of the medical instrument 28 until suitable calibration is performed. In some embodiments, the robotic medical procedure system 20 may be implemented when the position sensor 32 is integrated with the medical instrument 28 and/or the position of the position sensor 32 with respect to the distal end 34 of the medical instrument 28 is already known. In other embodiments, the position sensor 32 may be disposed on the robotic arm 40 and in such a case the location of the position sensor 32 does not initially indicate the distal end 34 of the medical instrument 28 until suitable calibration is performed.

Figure 3:
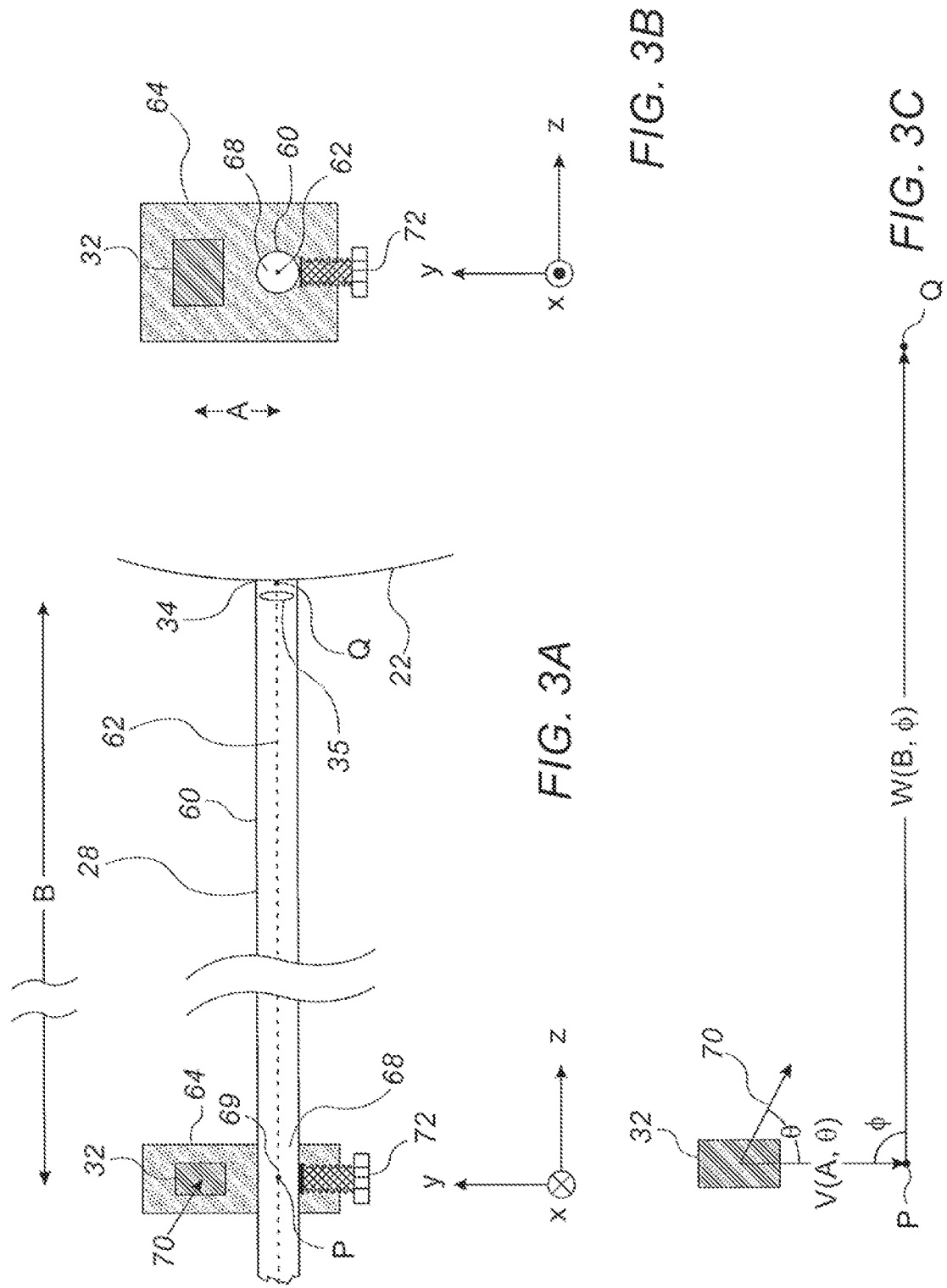
FIG. 3A is a schematic cross-sectional side view of an exemplary medical instrument.
FIG. 3B is a schematic cross-sectional front view of the medical instrument of FIG. 3B.
FIG. 3C is a schematic diagram illustrating vectors related to the medical instrument of FIGS. 3A and 3B, according to an embodiment of the present invention.

FIG. 3A is a schematic cross-sectional side view of the medical instrument 28, FIG. 3B is a schematic cross-sectional front view of the medical instrument 28, and FIG. 3C is a schematic diagram illustrating vectors related to the medical instrument 28, according to an embodiment of the present invention. In the following description of the medical instrument 28, the medical instrument 28 is assumed to comprise a rigid cylinder 60, having a longitudinal symmetry axis 62. In FIGS. 3A and 3B the medical instrument 28 has been drawn on a set of xyz orthogonal axes, with the longitudinal symmetry axis 62 defining the z-axis. For clarity, in FIGS. 3A and 3B the xyz axes of the medical instrument 28 are drawn displaced from the cylinder 60.

The position sensor 32 is fixed to the cylinder 60 by a sensor holder 64, which is typically formed from plastic so as to completely encapsulate the position sensor 32. As explained herein, signals from the position sensor 32, generated in response to the magnetic fields interacting with the position sensor 32, are used to determine a location and an orientation of the position sensor 32. Conducting wires that convey the signals from the position sensor 32 may be connected to the proximal end 52 of the medical instrument 28, and from there to the console 50. The conducting wires are not shown in FIGS. 3A and 3B.

The position sensor 32 is assumed to have a sensor direction 70, typically, but not necessarily, the direction of an internal axis of symmetry of the position sensor 32, and the orientation referred to herein measures the orientation of the sensor direction with respect to a frame of reference defined by the magnetic field radiators 26 (FIG. 2). The sensor direction 70 of the position sensor 32 is shown schematically in FIGS. 3A and 3C as an arrow.

The sensor holder 64 is produced to have a hole 68, which is formed to have a diameter substantially the same as that of cylinder 60, but sufficiently different so that there is a sliding fit between the holder 64 and the cylinder 60. When the holder 64 is produced, a center of the hole 68 is made to be a known distance A from the position sensor 32. A typical value of A is 0.5 cm, but A may be smaller or larger than this value. A series of sensor holders may be constructed, having holes that are dimensioned to medical instruments having different diameters. In addition, by virtue of being comprised in the holder 64, the center of the hole 68 has a known orientation θ with respect to the sensor direction 70. There is thus a known displacement vector (A, θ), herein also termed vector V, from the position sensor 32 to the center of the hole 68, as shown in FIG. 3C.

The hole 68 has an axis of symmetry 69 that is typically orthogonal to the vector V, and which by virtue of being formed when the holder 64 is produced, has a known direction φ with respect to the vector V (FIG. 3C).

As is also described below, in operating the system 20, the hole 68 of the sensor holder 64 is slid onto cylinder 60, and the holder 64 is fixed to the cylinder 60 when the holder 64 is close to the proximal end 52. It will be understood that in sliding the cylinder 60 within the hole 68, the axes 69 and 62 are coincident, and also coincide with direction φ. The holder 64 comprises a setscrew 72, having a head, which may be grasped by the physician 54 (FIG. 1). Using the head, the physician 54 is able to hand-tighten the setscrew to fix the holder 64 at a desired position along the cylinder 60. The distance from the center of the position sensor 32 to the distal end 34 is assumed to be a distance B. Unlike distance A, distance B is not known when sensor holder 64 is fixed to cylinder 60, but as is described below in operation of system 20, the controller 38 is able to calculate distance B.

FIG. 3A also shows a force sensor 35 disposed on, or embedded in, the medical instrument 28. The force sensor 35 is configured to provide a signal which is indicative of a force applied by the medical instrument 28 on the body-part. More than one force sensor 35 may be disposed at different lateral positions along the medical instrument 28 to provide force readings at different locations on the medical instrument 28. U.S. Patent Application Publications 2007/0100332 and 2009/0093806, whose disclosures are incorporated herein by reference, describe methods of sensing contact pressure between the distal tip of a catheter and tissue in a body cavity using a force sensor embedded in the catheter. In addition, the Carto® SmartTouch™ system produced by Biosense Webster of 33 Technology Drive, Irvine, Calif. 92618 USA, includes force sensors appropriate for the robotic medical procedure system 20.

Figure 4:
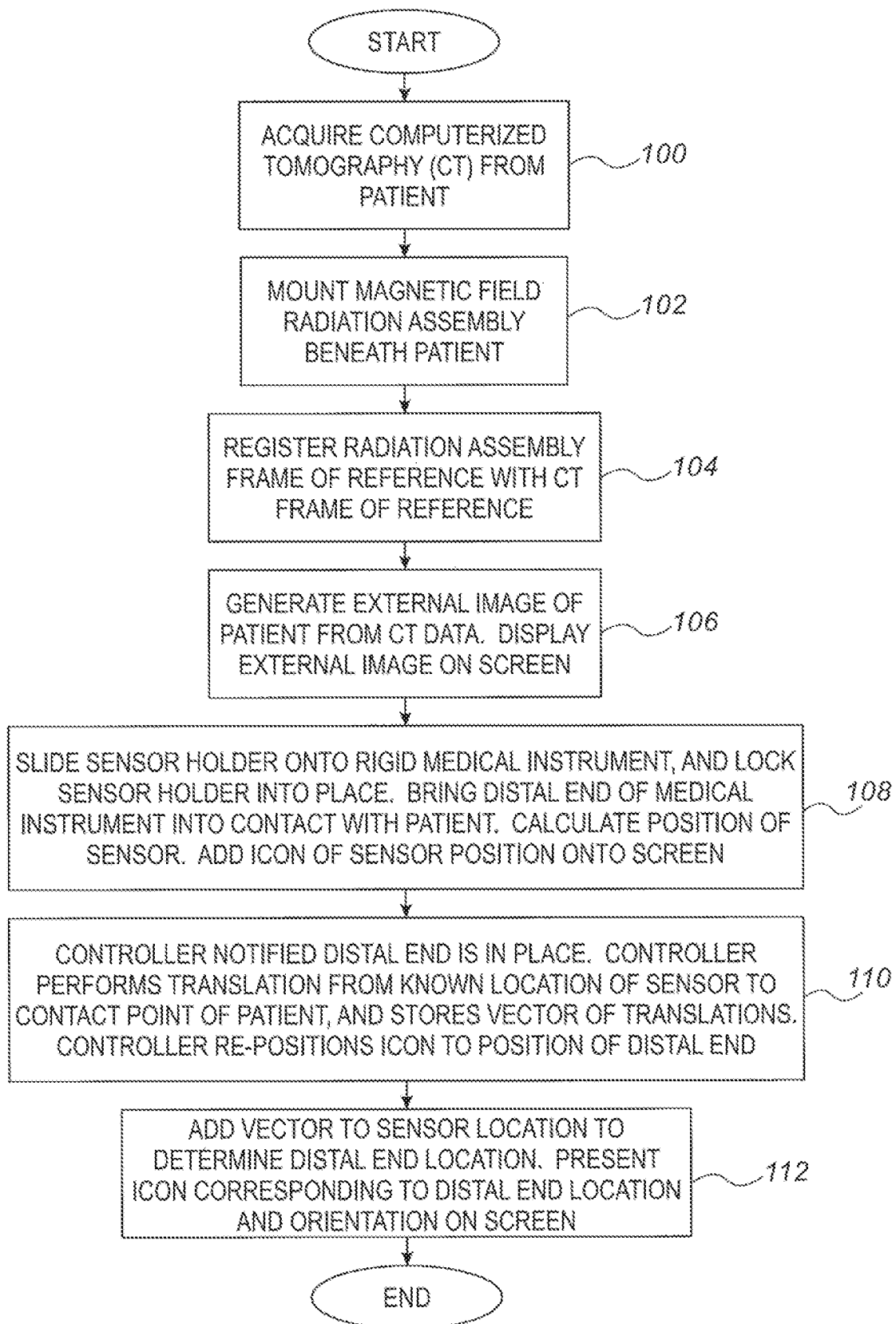
FIG. 4 is a flowchart including exemplary steps that are implemented in the operation of the robotic medical procedure system of FIG. 1, according to an embodiment of the present invention.
Figure 5:
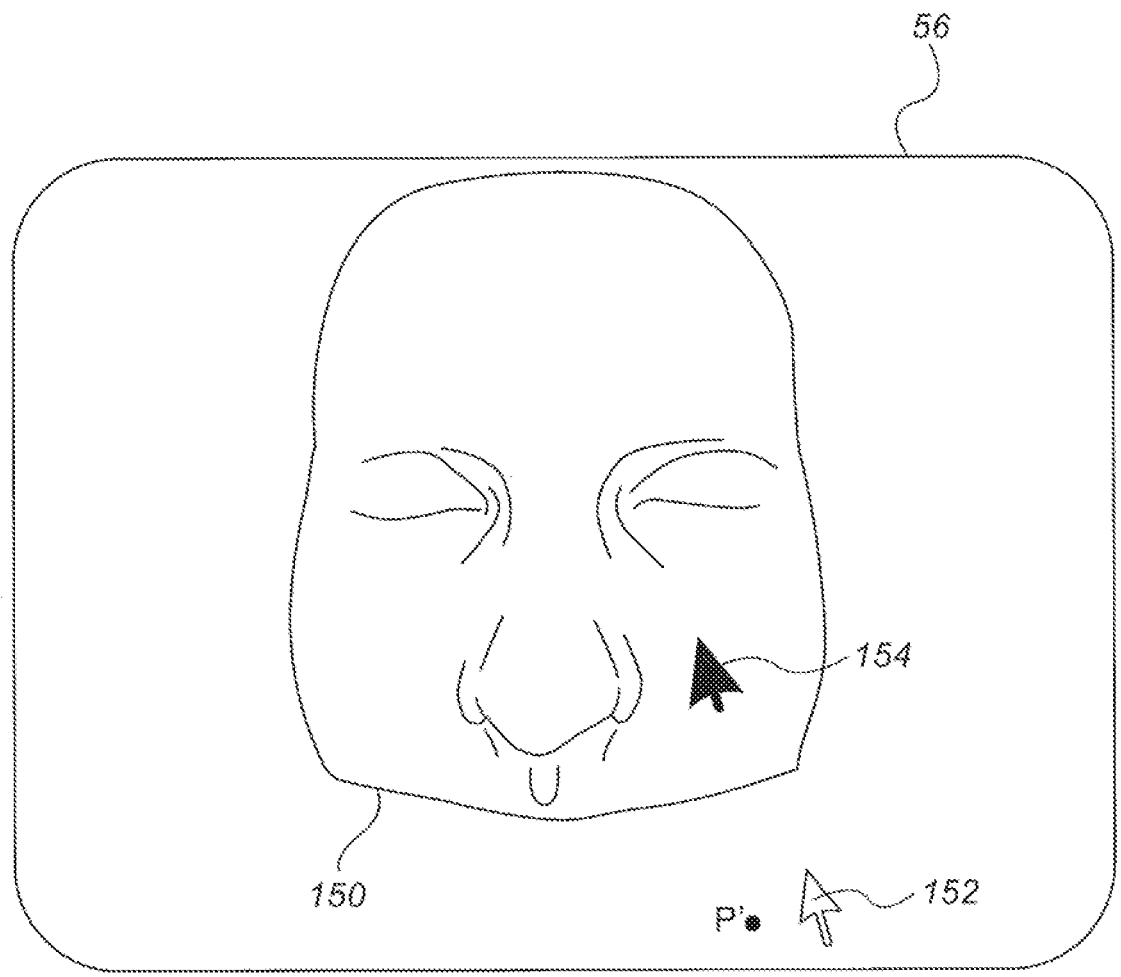
FIG. 5 is a schematic illustration of a screen used during implementation of the flowchart, according to an embodiment of the present invention.

FIG. 4 is a flowchart including exemplary steps that are implemented in the operation of the robotic medical procedure system 20, and FIG. 5 is a schematic illustration of the display screen 56 during implementation of the flowchart, according to an embodiment of the present invention. The steps of the flowchart are also illustrated by FIGS. 1, 2, 3A, 3B, and 3C.

In an initial step 100, the head of patient 22 is scanned by computerized tomography (CT), herein by way of example assumed to be fluoroscopic CT, and the CT data from the scan is acquired by controller 38. The CT scan of patient 22 may be performed independently of the implementation of the remaining steps of the flowchart, which correspond to the medical procedure. Typically, step 100 may be performed a number of days before the following steps of the medical procedure. In some embodiments, any other suitable medical scan may supplement or replace the CT scan.

In a first procedure step 102, the radiation assembly 24 is mounted beneath or behind the head of the patient 22. Radiators 26 are then operated, and in a registration step 104, a frame of reference of the radiators 26 is registered with the frame of reference of the subject's head. The registration is typically performed by any means known in the art, e.g., by placing a magnetic field sensor coil such as the position sensor 36, or a grouping of such coils, in one or more known locations and orientations with respect to the external features of the patient 22 as well as with the magnetic field radiation assembly 24 holding the radiators 26. Generally, in this step, the controller 38 is configured to register the CT data (or other medical scan) with respect to at least one given location of the body-part (e.g., the external features of the patient 22).

In an initial display step 106, controller 38 generates a representation 150, also referred to herein as image 150, of external features of the patient 22, using the CT data received in step 100. The CT data is in the form of voxels with Hounsfield units (HU), and the image 150 of the external features of patient 22 is generated from voxel values and their HU values. The image 150 is typically a gray scale image. The values of the gray scales, from black to white, may be correlated with the Hounsfield unit (HU) of the corresponding voxels.

The HU values are radiodensity values and as is known in the art, apart from the values for air and water, which by definition are respectively −1000 and 0, the value of the Hounsfield unit of any other substance or species, such as dense bone, is dependent, inter alia, on the spectrum of the irradiating X-rays used to produce the CT scans referred to herein. In turn, the spectrum of the X-rays depends on a number of factors, including the potential in kV applied to the X-ray generator, as well as the composition of the anode of the generator. For clarity in the present disclosure, the values of Hounsfield units for a particular substance or species are assumed to be as given in Table I below.

TABLE I

| Species/Substance | Hounsfield Unit |
| --- | --- |
| Air | −1000 |
| Soft Tissue | −300 to −100 |
| Fat | −50 |
| Water | 0 |
| Blood | +30 to +45 |
| Dense Bone | +3000 |

However, the numerical values of HUs for particular species (other than air and water) as given in Table I are to be understood as being purely illustrative, and those having ordinary skill in the art will be able to modify these illustrative values, without undue experimentation, according to the species and the X-ray machine used to generate the CT images referred to herein. Typically, a translation between HU values and gray scale values is encoded into a DICOM (Digital Imaging and Communications in Medicine) file that is the CT scan output from a given CT machine.

The controller 38 displays image 150 on the display screen 56, and FIG. 5 schematically illustrates the image 150 as displayed on the display screen 56.

The HU values also provide an indication of the different tissue types (e.g., bone, soft tissue, fat, blood) at different locations in the CT images. Registration of the CT scan with the robotic medical procedure system 20 may enable an anatomical feature next to the medical instrument 28 to be identified based on the HU values of the voxels at the location of the medical instrument 28. For example, soft tissue may be identified as being at the distal end 34 of the medical instrument 28 based on the HU values in the CT scan at the location of the distal end 34. Alternatively, dense bone may be identified in the CT scan based on the HU values near the distal end 34. Other anatomical features may be identified either automatically (using image analysis techniques) or manually (by a trained operator or radiologist) from analysis of the CT scan. The identified anatomical features may then be registered with the robotic medical procedure system 20 for use during a medical procedure. Therefore, different anatomical features may be identified as being close to the distal end 34, or another location of the medical instrument 28, when the medical instrument 28 is inserted in the body-part. The medical instrument 28 may be controlled to avoid applying excessive force to anatomical features based on a sensitivity of the anatomical features. For example, the optic nerve may be identified in the CT scan automatically, or by a radiologist, and then registered with the robotic medical procedure system 20 for use during a medical procedure. The medical instrument 28 may be controlled to avoid applying excessive force to the optic nerve when the medical instrument 28 is at the location of the optic nerve. These features are described in more detail with reference to FIG. 6.

In an operation step 108, the physician slides hole 68 of the sensor holder 64 onto the rigid cylinder 60 of the medical instrument 28, and the physician 54 then uses setscrew 72 to lock the sensor holder in place, near proximal end 52 of the medical instrument 28. Once the holder 64 is locked in place, the robotic arm 40 is set into loose mode that allows manual movement of the robotic arm 40 by the physician 54. The physician 54 brings the distal end 34 of the medical instrument 28 into contact with a selected region of the external features of the patient 22, for example a region at the side of the patient's nose.

The positioning of the distal end 34 brings the sensor holder 64 and its encapsulated position sensor 32 into the region 30, so that the controller 38 is able to calculate the location and orientation of the position sensor 32. Once the controller 38 has performed this calculation, it typically introduces an icon 152, representative of sensor direction 70, onto the display screen 56, in proximity to image 150. The icon 152 is located and orientated on the display screen 56 in accordance with the location and orientation of the position sensor 32, determined from the sensor signals, within the common frame of reference of the image 150 and the magnetic field radiators 26.

By virtue of the fact that the physician 54 is manipulating the medical instrument 28, the physician 54 is aware of the actual location and orientation of the position sensor 32. Comparison of the location and orientation of icon 152 with the actual location and orientation of position sensor 32 provides confirmation to the physician 54 of the correct operation of the robotic medical procedure system 20.

In a calibration step 110, the physician 54 notifies the controller 38 that the distal end 34 of the medical instrument 28 is in contact with an external feature of the patient 22, typically by using controls 51. On receipt of the notification, the controller 38 performs two translations on the known location of the position sensor 32. A first translation corresponds to vector V (A, θ), (FIG. 3C) so that the controller 38 translates the location of the position sensor 32 by a value A along a direction defined by θ to a point P on axis 62 (FIG. 3A). A point P', corresponding to point P, is drawn in FIG. 5, to illustrate the termination of the first translation. Typically, point P' is not drawn on screen 56.

From point P, the controller 38 performs a second translation, in a direction corresponding to direction ϕ. Since the axes 69 and 62 are coincident, the second translation is in a direction corresponding to translating along the axis 62. The controller 38 uses the data for the image 150 to determine the actual length of the second translation, by determining from the image data where point P, moving in direction ϕ along axis 69, meets an external surface of patient 22. The meeting with the external surface occurs when there is at least a predetermined change in radiodensity as measured in the image, e.g., a change in the value of the Hounsfield units of the image data. Suitable values for the change are 200-500 Hounsfield units. The meeting is assumed to be at a point Q on axis 62. Point Q is at a distance B, now known, from point P, and the second translation thus corresponds to a vector (B, ϕ), herein also termed vector W, and illustrated in FIG. 3C.

It will be understood that even though the calculation of the position of point Q uses CT image data, since the image 150 is registered with the actual external features of patient 22, point Q corresponds with an actual external point of the patient 22.

At the conclusion of the calibration step, the controller 38 deletes icon 152 from screen 56, and positions an icon 154 at a position on the image 150 corresponding to point Q. Comparison of the location and orientation of the icon 154 with the actual location and orientation of the distal end 34 provides confirmation to the physician 54 of the correct completion of the calibration step.

The sum of the two translations, V+W, of the calibration step is a vector that is stored by the controller 38.

In a continuing tracking step 112, the controller 38 adds the vector stored in step 110 to the location of the position sensor 32 in order to determine the location of distal end 34.

The orientation of the distal end 34 corresponds to direction φ, which is also determined by the controller 38 in tracking the position sensor 32. Thus, the controller 38 is able to calculate the location and orientation of the distal end 34 by computing the location and orientation of the position sensor 32. The controller 38 may position an icon corresponding to the location and orientation of the distal end 34 on the display screen 56. In some embodiments, if the distal end 34 is within patient 22, the external features of image 150 that may obscure the icon are rendered at least partially transparent. The position of the distal end 34 with respect to anatomic features of the patient 22 may be derived based on the calculated position of the distal end 34 with respect to coordinates on the registered image. In the above manner the distal end 34 of the medical instrument 28 may be guided into the body-part of the patient 22 to a desired location by observation the movement of the icon in the captured CT or other images.

In some embodiments, the distal end 34 of the medical instrument 28 may be guided in to the body-part automatically by the robotic arm 40 based on a suitable path-finding algorithm. An example algorithm is described with reference to US Published Patent Application No. 2017/0056112A1 of Gliner, et al. which is herein incorporated by reference.

Figure 6:
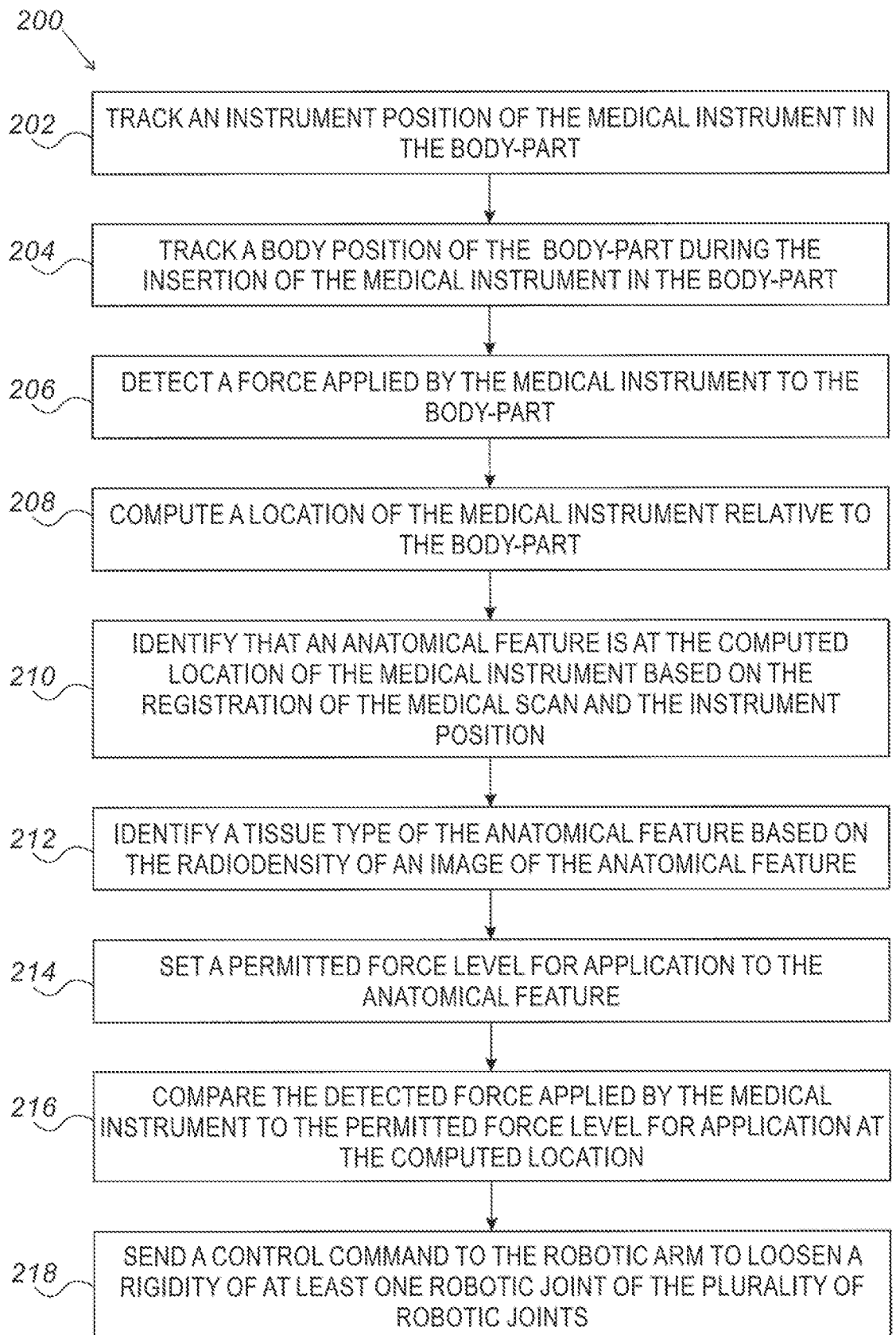
FIG. 6 is a flowchart including exemplary steps in a method for use in the robotic medical procedure system of FIG. 1.

Reference is now made to FIG. 6, which is a flowchart 200 including exemplary steps in a method for use in the robotic medical procedure system 20 of FIG. 1. Reference is also made to FIG. 1.

As described above with reference to FIG. 4, The HU values of the CT scan provide an indication of the different tissue types (e.g., bone, soft tissue, fat, blood) or other substances (e.g., water) at different locations in the CT images. Registration of the CT scan with the robotic medical procedure system 20 may enable an anatomical feature next to the medical instrument 28 to be identified based on the HU values of the voxels at the location of the medical instrument 28. For example, soft tissue may be identified as being at the distal end 34 of the medical instrument 28 based on the HU values in the CT scan at the location of the distal end 34. Alternatively, dense bone may be identified in the CT scan based on the HU values near the distal end 34. Other anatomical features may be identified either automatically (using image analysis techniques) or manually (by a trained operator or radiologist) from analysis of the CT scan. The identified anatomical features may then be registered with the robotic medical procedure system 20 for use during a medical procedure. For example, the optic nerve may be identified in the CT scan automatically or by a radiologist and then registered with the robotic medical procedure system 20. The medical instrument 28 may be controlled to avoid applying excessive force to the optic nerve when the medical instrument 28 is at the location of the optic nerve.

The position sensor 32 is configured to track (block 202) an instrument position of the medical instrument 28 in the body-part. The position sensor 36 is configured to track (block 204) a body position of the body-part during the insertion of the medical instrument 28 in the body-part. The force sensor 35 (FIG. 3A) is configured to detect (block 206) a force applied by the medical instrument 28 to the body-part.

The controller 38 is configured to compute (block 208), responsively to the instrument position and the body position, a location of the medical instrument 28 relative to the body-part.

The controller 38 is configured to identify (block 210) that an anatomical feature is at the computed location of the medical instrument 28 based on the registration of the medical scan and the instrument position. For example, the controller 38 identifies a location in the CT scan corresponding with the computed location of the medical instrument 28. The location of the CT scan may include an anatomical feature. The anatomical feature may be a tissue type which is identified in step 212 below. Additionally, or alternatively, the anatomical feature may be an organ or nerve or other feature that was identified in the CT scan automatically (e.g., using image analysis) or by a radiologist and then registered with the robotic medical procedure system 20 prior to the medical procedure.

The controller 38 is configured to identify (block 212) a tissue type (e.g., bone, soft tissue, blood, fat) of the anatomical feature based on the radiodensity (e.g., HU value) of the image of the anatomical feature. Additionally, or alternatively, the controller 38 is configured to identify (block 212) an identification of the anatomical feature (e.g., the optic nerve or brain) based on an identification of the anatomical feature that was registered with the robotic medical procedure system 20 prior to the medical procedure.

The controller 38 is configured to set (block 214) a permitted force level for application to the anatomical feature. In some embodiments, the controller 38 is configured to set the permitted force level for application to the anatomical feature based on a known or estimated sensitivity and/or importance of the anatomical feature. For example, the optic nerve may be more important than another nerve. In some embodiments, the controller 38 is configured to set the permitted force level for application to the anatomical feature based on a sensitivity and/or importance of the tissue type of the anatomical feature. For example, soft tissue is more sensitive than hard bone. In some embodiments, the controller 38 is configured to set the permitted force level for application to the anatomical feature based on the radiodensity (e.g., HU value) of the image of the anatomical feature. By way of example only, the permitted force level may be set to 2 gram-force (gmf) for tissue surrounding the eye orbit, less than 1 gmf for the optic nerve, and 30 gmf for nasal bone, where 1 gmf is equivalent to the weight of 1 gram of mass at standard gravity.

The controller 38 is configured to compare (block 216) the detected force applied by the medical instrument 28 to a permitted force level for application to the anatomical feature at the computed location. If the medical instrument 28 includes multiple force sensors 35, the reading from the force sensors 35 may be averaged. Additionally, or alternatively, the readings from the different force sensors 35 may be processed individually by the controller 38 wherein the controller 38 compares the detected force at the location of each respective force sensor 35 with the permitted force level for the anatomical feature adjacent to each of the respective force sensors 35.

The controller 38 is configured to send (block 218) a control command to, or cut power of, the robotic arm 40 to loosen a rigidity of at least one robotic joint of the plurality of robotic joints of the robotic arm 40 in response to the detected force applied by the medical instrument 28 at the computed location being greater than the permitted force level. The loose mode may even lead to the robotic arm 40 dropping the medical instrument 28, but this is acceptable compared to the risk of trauma if there is still feedback to the actuators of the robotic arm 40. In some embodiments, the controller 38 is configured to send a control command to the robotic arm 40 to drop the medical instrument 28 in response to the detected force applied by the medical instrument 28 at the computed location being greater than the permitted force level.

Various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination.

The embodiments described above are cited by way of example, and the present invention is not limited by what has been particularly shown and described hereinabove. Rather the scope of the invention includes both combinations and subcombinations of the various features described hereinabove, as well as variations and modifications thereof which would occur to persons skilled in the art upon reading the foregoing description and which are not disclosed in the prior art.

What is claimed is:

1. A robotic arm control system comprising:
   a medical instrument configured to be reversibly inserted into a body-part of a living subject;
   a force sensor configured to detect a force applied by the medical instrument to the body-part;
   a robotic arm attached to the medical instrument, the robotic arm including a plurality of robotic joints configured to control movement of the robotic arm and manipulate the medical instrument;
   a first position sensor configured to track an instrument position of the medical instrument in the body-part;
   a second position sensor disposed on the living subject and configured to track a body position of the body-part during the insertion of the medical instrument in the body-part; and
   a controller configured to:
     compute, responsively to the instrument position and the body position, a location of the medical instrument relative to the body-part;
     compare the detected force applied by the medical instrument to a permitted force level for application to an anatomical feature at the computed location; and
     send a control command to, or cut power of, the robotic arm to loosen a rigidity of at least one robotic joint of the plurality of robotic joints in response to the detected force applied by the medical instrument at the computed location being greater than the permitted force level.

2. The system according to claim 1, wherein the force sensor is disposed on the medical instrument.

3. The system according to claim 1, wherein the controller is configured to set the permitted force level for application to the anatomical feature.

4. The system according to claim 3, wherein the controller is configured to:
   register a medical scan with respect to at least one given location of the body-part, the medical scan including an image of the anatomical feature; and
   identify that the anatomical feature is at the computed location of the medical instrument based on the registration of the medical scan and the instrument position.

5. The system according to claim 4, wherein controller is configured to set the permitted force level for application to the anatomical feature based on an identification of the anatomical feature.

6. The system according to claim 4, wherein:
   the image of the anatomical feature has a radiodensity; and
   the controller is configured to set the permitted force level for application to the anatomical feature based on the radiodensity of the image of the anatomical feature.

7. The system according to claim 6, wherein the controller is configured to:
   identify a tissue type of the anatomical feature based on the radiodensity of the image of the anatomical feature; and
   set the permitted force level for application to the anatomical feature based on the tissue type of the anatomical feature.

8. The system according to claim 1, wherein the controller is configured to send a control command to the robotic arm to drop the medical instrument in response to the detected force applied by the medical instrument at the computed location being greater than the permitted force level.

9. A robotic arm control method comprising:
   controlling movement of a robotic arm attached to a medical instrument, which is reversibly inserted into a body-part of a living subject;
   detecting a force applied by the medical instrument to the body-part;
   tracking an instrument position of the medical instrument in the body-part;
   tracking a body position of the body-part during the insertion of the medical instrument in the body-part;
   computing, responsively to the instrument position and the body position, a location of the medical instrument relative to the body-part;
   comparing the detected force applied by the medical instrument to a permitted force level for application to an anatomical feature at the computed location; and
   sending a control command to, or cutting power of, the robotic arm to loosen a rigidity of at least one robotic joint of the robotic arm in response to the detected force applied by the medical instrument at the computed location being greater than the permitted force level.

10. The method according to claim 9, wherein the detecting the force is performed by a force sensor that is disposed on the medical instrument.

11. The method according to claim 9, further comprising setting the permitted force level for application to the anatomical feature.

12. The method according to claim 11, further comprising:
    registering a medical scan with respect to at least one given location of the body-part, the medical scan including an image of the anatomical feature; and
    identifying that the anatomical feature is at the computed location of the medical instrument based on the registration of the medical scan and the instrument position.

13. The method according to claim 12, wherein the setting the permitted force level for application to the anatomical feature is based on an identification of the anatomical feature.

14. The method according to claim 12, wherein:
    the image of the anatomical feature has a radiodensity; and
    the setting the permitted force level for application to the anatomical feature is based on the radiodensity of the image of the anatomical feature.

15. The method according to claim 14, further comprising identifying a tissue type of the anatomical feature based on the radiodensity of the image of the anatomical feature, and wherein the setting the permitted force level for application to the anatomical feature is based on the tissue type of the anatomical feature.

16. The method according to claim 9, wherein the sending includes sending a control command to the robotic arm to drop the medical instrument in response to the detected force applied by the medical instrument at the computed location being greater than the permitted force level.

17. A software product, comprising a non-transient computer-readable medium in which program instructions are stored, which instructions, when read by a central processing unit (CPU), cause the CPU to:
- control movement of a robotic arm attached to a medical instrument, which is reversibly inserted into a body-part of a living subject;
- store a detected force applied by the medical instrument to the body-part;
- store an instrument position of the medical instrument in the body-part;
- store a body position of the body-part during the insertion of the medical instrument in the body-part;
- compute, responsively to the instrument position and the body position, a location of the medical instrument relative to the body-part;
- compare the detected force applied by the medical instrument to a permitted force level for application to an anatomical feature at the computed location; and
- send a control command to, or cut power of, a robotic arm to loosen a rigidity of at least one robotic joint of the robotic arm in response to the detected force applied by the medical instrument at the computed location being greater than the permitted force level.

* * * * *